United States Patent [19]

Koppitsch et al.

[11] Patent Number: 4,931,741

[45] Date of Patent: * Jun. 5, 1990

[54] BRANCHED SENSOR SYSTEM

[75] Inventors: Heinrich Koppitsch, Ottobrunn, Fed. Rep. of Germany; Francis Sparling, Sunnyvale, Calif.

[73] Assignee: Raychem Corporation, Menlo Park, Calif.

[ * ] Notice: The portion of the term of this patent subsequent to May 30, 2006 has been disclaimed.

[21] Appl. No.: 287,366

[22] Filed: Dec. 20, 1988

Related U.S. Application Data

[63] Continuation-in-part of Ser. No. 57,459, Jun. 3, 1987, Pat. No. 4,843,327.

[30] Foreign Application Priority Data

May 31, 1988 [EP] European Pat. Off. ........ 88304957.9

[51] Int. Cl.⁵ .............................................. G01R 31/08
[52] U.S. Cl. .................................. 324/525; 174/11 R; 324/512; 324/693; 340/602; 379/26
[58] Field of Search ............ 324/525, 521, 509, 65 R, 324/512; 379/331, 26; 361/58, 42, 49; 340/602; 338/38; 174/11 R

[56] References Cited

U.S. PATENT DOCUMENTS

| | | | |
|---|---|---|---|
| 3,234,459 | 2/1986 | Brazee | 324/525 X |
| 3,248,646 | 4/1966 | Brazee | 324/525 X |
| 3,460,123 | 8/1969 | Bass | 340/602 X |
| 3,560,850 | 2/1971 | Hojding | 324/52 |
| 3,668,472 | 6/1972 | Shields et al. | 361/49 |
| 4,013,924 | 3/1977 | Christensen et al. | 361/49 |
| 4,442,422 | 4/1984 | Murata et al. | 73/29 X |

FOREIGN PATENT DOCUMENTS 0133748  3/1985  European Pat. Off. .
0160440  6/1985  European Pat. Off. .
0160441  6/1985  European Pat. Off. .

Primary Examiner—Reinhard J. Eisenzopf
Assistant Examiner—Robert W. Mueller
Attorney, Agent, or Firm—Timothy H. P. Richardson; Herbert G. Burkard

[57] ABSTRACT

A detection and location system, e.g. for liquid leaks, comprising a trunk line sensor cable and a plurality of branch line cables at intermediate points of the trunk cable. Each of the cables comprises two insulated conductors and two non-insulated conductors, e.g. conductive polymer-coated wires, which become connected upon occurrence of a leak. In one embodiment, each of the insulated conductors in the trunk line is continuous and each of the non-insulated conductors is discontinuous at each intermediate point; the branch line conductors are respectively connected to the discontinuous ends of the non-insulated trunk line conductors, and are connected in pairs of one insulated and one non-insulated conductor at the end of each branch. In another embodiment, in the trunk line, both the non-insulated conductors and one of the insulated conductors are continuous and one of the insulated conductors is discontinuous at each intermediate point; in the branch line, the two insulated conductors are respectively connected to the discontinuous ends of the insulated trunk line conductor at the intermediate point, and to each other at the end of the branch, and the two non-insulated conductors are respectively connected to the non-insulated trunk line conductors but are not otherwise connected.

14 Claims, 2 Drawing Sheets

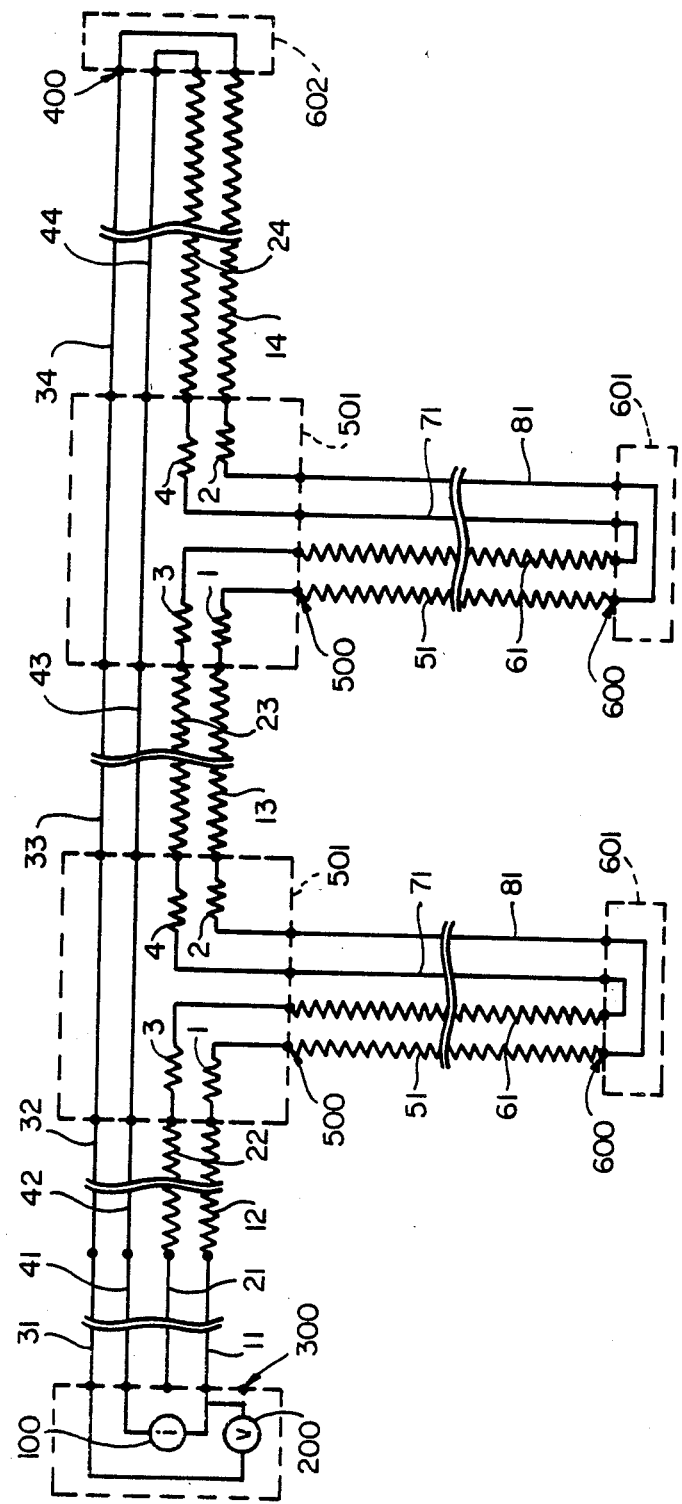
FIG_1

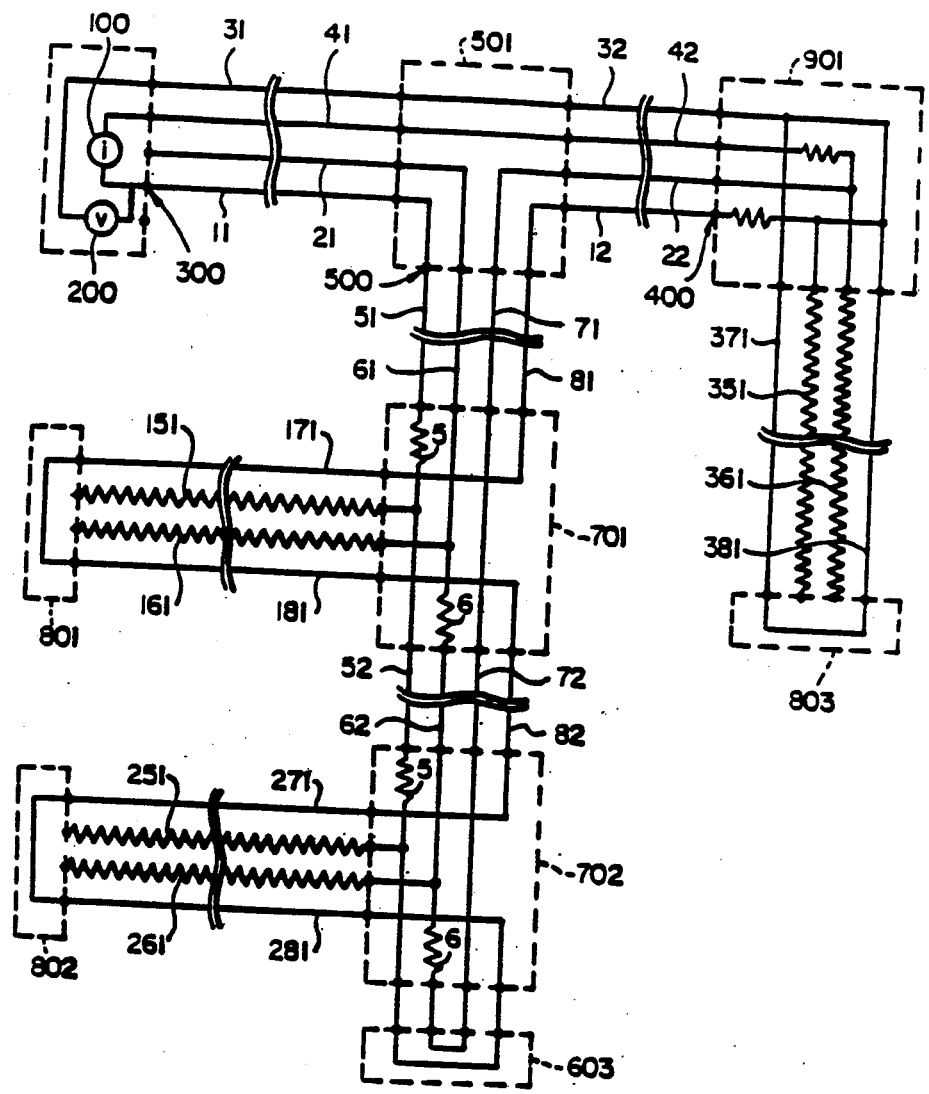
FIG_2

BRANCHED SENSOR SYSTEM

CROSS-REFERENCE TO RELATED APPLICATIONS

This application is a continuation-in-part of our co-pending commonly assigned application Ser. No. 057,459 filed June 3, 1987, now U.S. Pat. No. 4,843,327 the entire disclosure of which is incorporated herein by reference.

BACKGROUND OF THE INVENTION

Field of the Invention

This invention relates to methods and apparatus for detecting and locating changes in variables.

INTRODUCTION TO THE INVENTION

Copending, commonly assigned U.S. patent application Ser. No. 832,562, filed Feb. 20, 1986, by Masia et al., the disclosure of which is incorporated herein by reference, discloses methods and apparatus for detecting and obtaining information about (particularly locating) changes in variables. Such changes are referred to in that application, and likewise in this application, by the generic term "event". In a preferred embodiment of such methods, and in other methods, there is used a sensor cable comprising two insulated wires and two "non-insulated" wires which are not connected to each other at any point along the length of the cable in the absence of an event but which become electrically connected to each other at some point along the length of the cable upon occurrence of an event. The non-insulated wires can for example comprise a metal core surrounded by a conductive polymer jacket, so that the wires become electrically connected if there is a water leak. The term "conductive polymer" is used herein to denote a composition which comprises a polymeric component (e.g. a thermoplastic, or an elastomer, or a mixture of two or more such polymers) and, dispersed in the polymeric component, a particulate conductive filler (e.g. carbon black, graphite, a metal powder, or two or more of these). The possibility of connection can for example exist at all points along an elongate path, or over selected stretches of an elongate path, or at discrete locations along an elongate path; for example the non-insulated wires can be wires which are insulated except at spaced locations and which can become connected at one or more of those locations through a switch which is switched on by occurrence of an event at the location of that switch.

When such a four-wire sensor cable is used to detect events along a path comprising one or more branch paths extending from a main (or trunk) path, the cable can simply be routed along the branch path to the end of the branch path and then straight back to the trunk path. However, this can lead to misleading results, since an event taking place along the branch can cause connection of the non-insulated wires in both the outgoing branch cable and the incoming branch cable. This problem can be overcome by running the sensor cable from the junction of the trunk and branch paths to the end of the branch path only, and using four insulated "jumper" wires to make the appropriate connections from the end of the branch back to the trunk; but this is an expensive and inconvenient solution, especially when space is limited, e.g. in a double containment system.

SUMMARY OF THE INVENTION

We have now recognized that in a branched system using a four-wire sensor cable, the two insulated wires are not needed in the branch line to perform the functions for which they are needed when the four wire sensor cable is part of a trunk line, and that these insulated wires can, therefore, be used (a) as insulated jumper wires to connect the non-insulated wires between the junction of a branch and the end of a branch, or (b) can be connected to each other at the end of a branch and to incoming and outgoing ends of one of the insulated wires at the junction of a branch, thus providing a loop around the branch for continuity checking purposes.

In a first embodiment of the invention, the insulated wires of the trunk cable are simply connected to each other across the junction; the non-insulated wires of the branch are connected (a) at the junction, to the non-insulated wires coming into (or going out of) the junction along the trunk path, and (b) at the end of the branch, to the insulated wires of the branch; and the insulated wires of the branch are connected at the junction to the non-insulated wires going out of (or coming into) the junction along the trunk path. In this way the errors which can occur with a simple loop system are substantially reduced or eliminated, as is the expense of the return leg of the four-wire sensor cable, or the inconvenience and expense of using separate jumper wires. Furthermore, the connections which have to be made at the end of the branch line can be the same as those made at the end of the trunk line, so that the same termination apparatus can be used.

Accordingly, in one aspect, the present invention provides a sensor cable suitable for use in detecting and obtaining information about an event, the apparatus comprising (1) a trunk line cable which follows an elongate trunk path having a near end and a far end; and (2) at least one branch line cable which extends from the trunk line cable at an intermediate point along the trunk path and follows an elongate branch path from the intermediate point to a distant point;

the trunk line cable comprising first, second, third and fourth elongate electrically conductive members, each of the first and second members running along the whole length of the trunk path but being discontinuous at each intermediate point to provide an incoming end nearer to the near end of the trunk path and an outgoing end nearer to the far end of the trunk path, and each of the third and fourth members running continuously along the whole length of the trunk path;

the branch line cable comprising fifth, sixth, seventh and eighth elongate electrically conductive members, each of which runs continuously along the whole length of the branch path and has a first end at the intermediate point and a second end at the distant point;

each of the first ends of the fifth, sixth, seventh and eighth members being respectively connected to one of the incoming and outgoing ends of the first and second members, the second ends of the fifth and sixth members being respectively connected to the second ends of the seventh and eighth members, so that the incoming and outgoing ends of the first member are electrically connected to each other through the branch line cable and the incoming and outgoing ends of the second member are electrically connected to each other through the branch line cable;

the first and second members being, in the absence of an event, insulated from each other and from other components of the trunk line cable along the length of the trunk line cable except for said connections at each intermediate point, and optionally being such that upon occurrence of an event at a point along the trunk path, electrical connection is made between the first and second members at that point;

the third and fourth members being such that they are electrically insulated from each other and from other components of the trunk line cable along the length of the trunk line cable, both in the absence of an event and upon occurrence of an event;

the fifth and sixth members being, in the absence of an event, insulated from each other and from other components of the branch line cable along the length of the branch line cable, except for said connections at each intermediate point and distant point, and being such that upon occurrence of an event at a point along the branch path, electrical connection is made between the fifth and sixth members at that point; and the seventh and eighth members being such that, both in the absence of an event and upon occurrence of an event, they are electrically insulated from each other and from other components of the branch line cable along the length of the branch line cable, except for said connections at each intermediate point and distant point.

In a second embodiment of the invention, wherein a four-wire sensor cable provides branches for detection of an event (and for location of the branch along which the event has occurred, but not for identifying the point along the branch at which the event occurred), there is provided a sensor cable for use in detecting and obtaining information about an event, the cable comprising (1) a trunk line cable which follows an elongate trunk path having a near end and a far end; and (2) at least one branch line cable which extends from the trunk line cable at an intermediate point along the trunk path and follows an elongate branch path from the intermediate point to a distant point;

the trunk line cable comprising first, second, third and fourth elongate electrically conductive members, each of the first and second members running continuously along the whole length of the trunk path, one of the third and fourth members running continuously along the whole length of the trunk path, and the other of the third and fourth members running along the whole length of the trunk path but being discontinuous at each intermediate point to provide an incoming end nearer to the near end of the trunk path and an outgoing end nearer to the far end of the trunk path;

the branch line cable comprising fifth, sixth, seventh and eighth elongate electrically conductive members, each of which runs continuously along the whole length of the branch path and has a first end at the intermediate point and a second end at the distant point;

the first end of the fifth member being connected to the first member at the intermediate point, the first end of the sixth member being connected to the second member at the intermediate point, the first end of the seventh member being connected to the incoming end of the third or fourth member, the first end of the eighth member being connected to the outgoing end of the third or fourth member, and the second ends of the seventh and eighth members being connected to each other at the distant point;

the first and second members being, in the absence of an event, insulated from each other and from other components of the trunk line cable along the length of the trunk line cable, except for said connections at each intermediate point, and optionally being such that upon occurrence of an event at a point along the trunk path, electrical connection is made between the first and second members at that point;

the third and fourth members being such that they are electrically insulated from each other and from other components of the trunk line cable along the length of the trunk line cable, except for said connections at each intermediate point, both in the absence of an event and upon occurrence of an event;

the fifth and sixth members being, in the absence of an event, insulated from each other and from other components of the branch line cable along the length of the branch line cable, except for said connections at each intermediate point, and being such that upon occurrence of an event at a point along the branch path, electrical connection is made between the fifth and sixth members at that point; and the seventh and eighth members being such that, both in the absence of an event and upon occurrence of an event, they are electrically insulated from each other and from other components of the branch line cable along the length of the branch line cable, except for said connections at each intermediate point and distant point.

The novel sensor cables of the invention preferably form part of an apparatus for detecting and locating an event which comprises (A) a power source;
(B) a voltage measuring device, and
(C) a sensor cable as defined above.

In the case of a sensor cable according to the first embodiment of the invention, for example, the apparatus is preferably such that, upon occurrence of an event at a location along the cable, an electrical connection is made at that location either between the first and second members or between the fifth and sixth members; and the making of said connection resulting in a system in which (i) the first member is electrically connected (a) at the near end of the trunk path, to the power source and to the voltage-measuring device, and (b) at the far end of the trunk path, to the third member;

(ii) the third member is electrically connected (a) at the near end of the trunk path, to the voltage-measuring device, and (b) at the far end of the trunk path, to the first member;

(iii) the fourth member is electrically connected (a) at the near end of the trunk path, to the power source, and (b) at the far end of the trunk path, to the second member;

(iv) there is a test circuit in which a current of known size flows and which comprises
 (a) those parts of the second, sixth and seventh members which lie between the connection point and the far end of the trunk path,
 (b) the connection;
 (c) those parts of the first, fifth and eighth members which lie between the connection point and the near end of the trunk path,
 (d) the fourth member of the trunk cable, and
 (e) the power source, and (v) there is a reference circuit which comprises
 (a) the first, fifth and eighth members, (b) the third member, and
(c) the voltage-measuring device;
whereby the voltage measured by the voltage-measuring device can be used to determine the location of the connection point. If desired, the apparatus can be such that, in the absence of an event, no current flows through any of the first to eighth elongate members. Alternatively, in the absence of an event, there can be a current which flows through one or more of the members, either continuously or intermittently, e.g. for checking continuity, preferably a current which is relatively low by comparison with the current of known size which flows in the test circuit.

In preferred apparatus of this kind, at all points on the sensor cable at which occurrence of an event can cause connection between the first and second members or the fifth and sixth members, the sum of (a) the resistances of the first, fifth and eighth members and any resistors in series therewith, between the near end and the connection point, and (b) the resistances of the second, sixth and seventh members and any resistors in series therewith, between the connection point and the far end, is substantially independent of the location of the connection point.

In order to achieve this result, it is preferred that
(i) the incoming ends of the first and second members at each intermediate point are connected to the first ends of the fifth and sixth members respectively, or to the first ends of the seventh and eighth members respectively;
(ii) the outgoing ends of the first and second members at each intermediate point are connected to the first ends of the eighth and seventh members respectively, or to the first ends of the fifth and sixth members respectively,
(iii) the second ends of the fifth and eighth members are connected at each distant point; and
(iv) the second ends of the sixth and seventh members being connected at each distant point.

The trunk line cable comprises first, second, third and fourth elongate electrically conductive members. For any segments of the trunk line along which detection of an event is not required, the cable can simply comprise four insulated wires which are of low resistance. For any extended segments along which detection of an event is required, the trunk line cable can comprise two low resistance insulated wires and two high resistance conductive-polymercoated wires which become electrically connected to each other if an event occurs, eg. a leak of water or another electrolyte, or a leak of a hydrocarbon or other organic fluid which causes swelling of a component in the cable, thus effecting electrical connection; the high resistance wires are preferably identical and have a resistance per unit length which is substantially invariable under the operating conditions. The trunk line cable can also comprise spaced-apart locations at which connection between the source and locating members takes place upon occurrence of an event, eg. through the operation of switch. One form of switch is a pair of conductive-polymer-coated wires which extend from the trunk cable; one wire is connected to the source member and the other to the locating member. The pair of wires can be part of a zone cable which extends from the trunk cable and which comprises in addition two insulated low resistance wires which are connected as a loop to form part of the return member and thus enable the continuity of the system to be checked. Other possible features of the branch line cable are described in patent application Ser. No. 057,459.

The branch line cable can have the same characteristics as are described above for the trunk line cable, except that at least part of the branch line comprises members which, upon occurrence of an event, become electrically connected. However, the invention is particularly useful when the branch line cable comprises two low resistance insulated wires (which may be the same or different) and two conductive-polymer-coated wires (which are preferably the same), particularly when at least part of the trunk line cable has substantially the same physical construction as the branch line cable. Particularly under such circumstances, it is preferred to put resistors in the connections between the conductive-polymer-coated wires; this results in discontinuities in the possible readings of the voltage-measuring device, so that despite a small error in the reading, the location of the event can be identified as being in the trunk line or branch line, as the case may be.

A very useful attribute of the apparatus of the present invention is that is can be assembled at an installation site from pre-terminated cables and preassembled connection and termination units which can be manufactured in a factory, thus eliminated the need to carry out in situ wiring, with the attendant risk of error. The various connection and termination units can be assembled (and if desired sealed) as flexible harnesses or in boxes.

BRIEF DESCRIPTION OF THE DRAWING

The invention is illustrated in the accompanying drawing, in which

FIG. 1 is a circuit diagram of an apparatus comprising a sensor cable according to the first embodiment of the invention, and FIG. 2 is a circuit diagram of an apparatus comprising a sensor cable according to the second emodiment of the invention.

DETAILED DESCRIPTION OF THE INVENTION

Referring now to the drawing, each of the Figures is a circuit diagram of an apparatus of the invention which comprises
(A) a constant current power supply (100);
(B) a high impedance voltmeter (200);
(C) a trunk line cable which has a near end (300) and a far end (400), and which is made up of a plurality of segments, each segment comprising a first member (11, 12, 13 etc.), a second member (21, 22, 23 etc.), a third member (31, 32, 33 etc.) and a fourth member (41, 42, 43 etc.); and
(D) at least one branch line cable which extends from an intermediate point (500) along the trunk path to a distant point (600) and which is made up of one or more segments, each segment comprising a fifth member (51, 52, 53 etc.), a sixth member (61, 62, 63 etc.), a seventh member (71, 72, 73 etc.) and an eighth member (81, 82, 83 etc.).

In each of the Figures, the phantom lines enclose components which can conveniently be preassembled in a manufacturing facility (eg. as a box or a flexiblle harness), with appropriate connecting means for the cables which make up the rest of the apparatus. The pre-assembled parts and the cables can then be assembled at the site of the installation.

Referring now to FIG. 1, this comprises a trunk line cable having two identical branch line cables connected thereto in accordance with the first embodiment of the invention. The segment of the trunk line cable closest to the near end 300 comprises four low resistance insulated wires 11, 21, 31 and 41 and extends along a path along which detection of an event is not required. The second, third and fourth segments of trunk line cable comprise two low resistance insulated wires 32, 33 and 34, and 42, 43 and 44, and two identical high resistance conductive-polymer-coated wires 12, 13 and 14, and 22, 23 and 24 which become connected to each other if an event occurs, e.g. a leak of water or a hydrocarbon. At each intermediate point 500, the trunk line cable and the branch line cable are connected to a preassembled T-connector 501 which will not detect occurrence of an event, which makes the connections shown, and which includes four identical resistors 1, 2, 3 and 4. The branch line cable has a single segment which runs from the intermediate point 500 to the distant point 600 and which has the same physical construction as the second segment of the trunk line cable and comprises two low resistance insulated wires 71 and 81 and two identical high resistance conductive-polymer-coated wires 51 and 61 which become connected to each other if an event occurs. At the distant point 600, the branch line cable is connected to a preassembled terminator 601 which makes the connections shown. The final segment of the trunk line cable is connected to a preassembled terminator 602 which makes the connections shown and which can be identical to terminator 601.

The wires 11, 12, 51 and 13, the resistors 1 and 2, and the connections between them together form a locating member. The wires 21, 22, 61 and 23, the resistors 3 and 4, and the connections between them together form a source member.

When the occurrence of an event causes a connection to be made at a single point along the trunk or branch line cables (i.e. between members 12 and 22, or members 51 and 61, or members 13 and 23), the voltage measured by the voltmeter depends upon the resistance of the locating member between the near end 300 and the connection point. Through knowledge of the resistance per unit length of the various components, or through prior mapping of the system, the measured voltage indicates the location of the event. The resistors 1, 2, 3 and 4 ensure that, despite a small error in the voltage measurement, an operator can distinguish between an event at an end of the trunk line cable close to a T-connector and an event at the end of a branch line cable close to a T-connector or at the end of a branch cable close to a terminator 601.

In FIG. 1, the connections in the T-connector are between members 51 and 12, 61 and 22, 71 and 23, and 81 and 13. However, since the members 71 and 81 have much lower resistance than the members 51 and 61, results which are substantially the same could be obtained by making the connections between 51 and 12 (as before), 81 and 13 (as before), 61 and 23, and 71 and 22; and results which are equally accurate, or substantially as accurate, but in which locations on the branch line were measured from the distant point instead of the intermediate point, could be obtained by making the connections between 12 and 71, 22 and 81, 51 and 23, and 61 and 13 (equally accurate) or between 12 and 71, 22 and 51, 81 and 23, and 61 and 13 (substantially as accurate).

FIG. 1 shows two branch lines, but there could be any number of branch lines.

Referring now to FIG. 2, this shows a system in accordance with the second embodiment of the invention which will detect the occurrence of an event in one of a plurality of zones, but not elsewhere, and will identify the zone in which the event took place, but will not identify the location of the event in the zone. Between the zones, both the trunk line cable and the branch line cable comprise four insulated low resistance wires. In each zone, a first conductivepolymer-coated wire extends from the locating member, and a second conductive-polymer-coated wire extends from the source member, close to but not touching the first wire; upon occurrence of an event anywhere in the zone, the first and second wires are brought into electrical contact, thus connecting the source and locating members. Resistors are placed in the locating member so that the voltage measured by the voltmeter identifies the zone in which an event has taken place, and balancing resistors are placed in the source member.

The segment of the trunk line cable closest to the near end 300 comprises four low resistance wires 11, 21, 31 and 41. At the intermediate point 500, the trunk line cable and the branch line cable are connected to a preassembled T-connector 501 which makes the connections shown. The first segment of the branch line cable has the same physical construction as the trunk line cable and contains four low resistance insulated wires, and is connected to a T-zone connector 701, which makes the connections shown between a zone cable and the first and second segments of the branch line cable, and which contains resistors 5 and 6. The zone cable has the same physical construction as the branch line cable of FIG. 1, and contains two low resistance insulated wires 171 and 181 and two conductive-polymer-coated wires 151 and 161. It is, however, connected differently both at the T-zone connector 701 and at the zone terminator 801; the wires 171 and 181 are connected as a loop between insulated wires 81 and 82 so that it is possible to make a continuity check of the zone cable. The second segment of the branch line cable likewise contains four insulated wires 52, 62, 72 and 82. The second segment is connected to another T-zone connector 702 which is the same as 701 and to which is connected a second zone cable comprising insulated wires 271 and 281 and conductivepolymer-coated wires 251 and 261 and terminating in zone terminator 802. Terminator 603, which can be the same as terminator 601 used in FIG. 1 makes the appropriate connections at the end of the branch line.

The second segment of the trunk line cable, comprising four insulated wires 12, 22, 32 and 42, is connected via an end zone connector 901 to a zone cable which is like that in the other zones, which comprises two insulated wires 371 and 381 and two conductive-polymer-coated wires 351 and 361, and which is connected to zone terminator 803.

We claim:
1. A sensor cable for use in detecting and obtaining information about an event, the cable comprising
  (1) a trunk line cable which follows an elongate trunk path having a near end and a far end; and
  (2) at least one branch line cable which extends from the trunk line cable at an intermediate point along the trunk path and follows an elongate branch path from the intermediate point to a distant point;

the trunk line cable comprising first, second, third and fourth elongate electrically conductive members, each of the first and second members running along the whole length of the trunk path but being discontinuous at each intermediate point to provide an incoming end nearer to the near end of the trunk path and an outgoing end nearer to the far end of the trunk path, and each of the third and fourth members running continuously along the whole length of the trunk path;

the branch line cable comprising fifth, sixth, seventh and eighth elongate electrically conductive members, each of which runs continuously along the whole length of the branch path and has a first end at the intermediate point and a second end at the distant point;

each of the first ends of the fifth, sixth, seventh and eighth members being respectively connected to one of the incoming and outgoing ends of the first and second members, the second ends of the fifth and sixth members being respectively connected to the second ends of the seventh and eighth members, so that the incoming and outgoing ends of the first member are electrically connected to each other through the branch line cable and the incoming and outgoing ends of the second member are electrically connected to each other through the branch line cable;

the first and second members being, in the absence of an event, insulated from each other and from other components of the trunk line cable along the length of the trunk line cable, except for said connections at each intermediate point, and optionally being such that upon occurrence of an event at a point along the trunk path, electrical connection is made between the first and second members at that point;

the third and fourth members being such that they are electrically insulated from each other and from other components of the trunk line cable along the whole length of the trunk line cable, both in the absence of an event and upon occurrence of an event;

the fifth and sixth members being, in the absence of an event, insulated from each other and from other components of the branch line cable along the length of the branch line cable, except for said connections at each intermediate point and distant point, and being such that upon occurrence of an event at a point along the branch path, electrical connection is made between the fifth and sixth members at that point; and the seventh and eighth members being such that, both in the absence of an event and upon occurrence of an event, they are electrically insulated from each other and from other components of the branch line cable along the length of the branch line cable, except for said connections at each intermediate point and distant point.

2. A cable according to claim 1 wherein (i) the incoming ends of the first and second members at each intermediate point are connected to the first ends of the fifth and sixth members respectively, or to the first ends of the seventh and eighth members respectively;

(ii) the outgoing ends of the first and second members at each intermediate point are connected to the first ends of the eighth and seventh members respectively, or to the first ends of the fifth and sixth members respectively, (iii) the second ends of the fifth and eighth members are connected at each distant point; and (iv) the second ends of the sixth and seventh members being connected at each distant point.

3. A cable according to claim 1 wherein the physical construction of at least a part of the trunk line cable is substantially identical to the physical construction of at least a part of the branch cable.

4. A cable according to claim 1 wherein the first, second, fifth and sixth members are substantially identical in physical construction.

5. A cable according to claim 1 wherein at least a part of each of the first, second, fifth and sixth members comprises a metallic wire which is electrically surrounded by a conductive polymer.

6. A cable according to claim 1 which further comprises four substantially identical resistors at each intermediate point, each resistor providing one of said connections between the first ends of fifth, sixth, seventh and eighth resistors and the incoming and outgoing ends of the first and second members respectively.

7. A cable according to claim 1 in which the trunk line cable comprises a plurality of preterminated lengths of cable, each length comprising a part of the first, second, third and fourth members; each branch line cable comprises a preterminated length of cable which comprises the fifth, sixth, seventh and eighth members; at each intermediate point, the preterminated lengths of the trunk line cable and the branch line cables are terminated by substantially identical termination units which are such that the elongate members can only be connected in an electrically correct arrangement; and the trunk line cable and the branch line cables are terminated by substantially identical termination units which are such that the elongate elements can only be connected in an electrically correct arrangement.

8. A sensor cable for use in detecting and obtaining information about an event, the cable comprising (1) a trunk line cable which follows an elongate trunk path having a near end and a far end; and (2) at least one branch line cable which extends from the trunk line cable at an intermediate point along the trunk path and follows an elongate branch path from the intermediate point to a distant point;

the trunk line cable comprising first, second, third and fourth elongate electrically conductive members, each of the first and second members running continuously along the whole length of the trunk path, one of the third and fourth members running continuously along the whole length of the trunk path, and the other of the third and fourth members running along the whole length of the trunk path but being discontinuous at each intermediate point to provide an incoming end nearer to the near end of the trunk path and an outgoing end nearer to the far end of the trunk path;

the branch line cable comprising fifth, sixth, seventh and eighth elongate electrically conductive members, each of which runs continuously along the whole length of the branch path and has a first end at the intermediate point and a second end at the distant point;

the first end of the fifth member being connected to the first member at the intermediate point, the first end of the sixth member being connected to the second member at the intermediate point, the first end of the seventh member being connected to the incoming end of the third or fourth member, the first end of the eighth member being connected to the outgoing end of the third or fourth member, and the second ends of the seventh and eighth members being connected to each other at the distant point;

the first and second members being, in the absence of an event, insulated from each other and from other components of the trunk line cable along the length of the trunk line cable, except for said connections at each intermediate point, and optionally being such that upon occurrence of an event at a point along the trunk path, electrical connection is made between the first and second members at that point;

the third and fourth members being such that they are electrically insulated from each other and from other components of the trunk line cable along the length of the trunk line cable, except for said connections at each intermediate point, both in the absence of an event and upon occurrence of an event;

the fifth and sixth members being, in the absence of an event, insulated from each other and from other components of the branch line cable along the length of the branch line cable, except for said connections at each intermediate point, and being such that upon occurrence of an event at a point along the branch path, electrical connection is made between the fifth and sixth members at that point; and the seventh and eighth members being such that, both in the absence of an event and upon occurrence of an event, they are electrically insulated from each other and from other components of the branch line cable along the length of the branch line cable, except for said connections at each intermediate point and distant point.

9. Apparatus suitable for use in detecting and locating an event, the apparatus comprising:
 (A) a power source;
 (B) a voltage measuring device; and
 (C) a sensor cable as claimed in claim 1
the apparatus being such that, upon occurrence of an event at a location along the sensor cable, an electrical connection is made at that location either between the first and second members or between the fifth and sixth members; and the making of said connection resulting in a system in which
 (i) the first member is electrically connected (a) at the near end of the trunk path, to the power source and to the voltage-measuring device, and (b) at the far end of the trunk path, to the third member;
 (ii) the third member is electrically connected (a) at the near end of the trunk path, to the voltage-measuring device, and (b) at the far end of the trunk path, to the first member;
 (iii) the fourth member is electrically connected (a) at the near end of the trunk path, to the power source, and (b) at the far end of the trunk path, to the second member;
 (iv) there is a test circuit in which a current of known size flows and which comprises
  (a) those parts of the second, sixth and seventh members which lie between the connection point and the far end of the trunk path,
  (b) the connection;
  (c) those parts of the first, fifth and eighth members which lie between the connection point and the near end of the trunk path,
  (d) the fourth member of the trunk cable, and
  (e) the power source, and
 (v) there is a reference circuit which comprises
  (a) the first, fifth and eighth members,
  (b) the third member, and
  (c) the voltage-measuring device;
whereby the voltage measured by the voltage-measuring device can be used to determine the location of the connection point.

10. Apparatus according to claim 9 wherein, at all points on the sensor cable at which occurrence of an event can cause connection between the first and second members or the fifth and sixth members, the sum of (a) the resistances of the first, fifth and eighth members and any resistors in series therewith, between the near end and the connection point, and (b) the resistances of the second, sixth and seventh members and any resistors in series therewith, between the connection point and the far end, is substantially independent of the location of the connection point.

11. A cable according to claim 8 wherein the first and second members are insulated from each other and from other components of the trunk line cable along the length of the trunk line cable both in the absence of an event and upon occurrence of an event along the length of the trunk line cable.

12. A cable according to claim 8 wherein at least a part of each of the fifth and sixth members comprises a metallic wire which is electrically surrounded by a conductive polymer.

13. A cable according to claim 8 which further comprises two substantially identical resistors at each intermediate point, one of the resistors forming part of the first member between the near end of the trunk line cable and the connection between the first member and the fifth member at the intermediate point, and the other resistor forming part of the second member between the connection between the second member and the sixth member.

14. A cable according to claim 8 in which the trunk line cable comprises a plurality of predetermined lengths of cable, each length comprising a part of the first, second, third and fourth members; each branch line cable comprises a preterminated length of cable which comprises the fifth, sixth, seventh and eighth members; at each intermediate point, the preterminated lengths of the trunk line cable and the branch line cables are terminated by substantially identical first termination units which are such that the elongate members can only be connected in an electrically correct arrangement; and the branch line cables are terminated by substantially identical second termination units which are such that the elongate members can only be connected in an electrically correct arrangement.

* * * * *